US009739706B2

(12) United States Patent
Maity et al.

(10) Patent No.: US 9,739,706 B2
(45) Date of Patent: Aug. 22, 2017

(54) METHOD AND SYSTEM FOR DETECTING A COMPONENT IN A FLUID

(71) Applicant: General Electric Company, Schenectady, NY (US)

(72) Inventors: Sandip Maity, Karnataka (IN); Nagapriya Kavoori Sethumadhavan, Karnataka (IN); Niloy Choudhury, Karnataka (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 151 days.

(21) Appl. No.: 14/467,136

(22) Filed: Aug. 25, 2014

(65) Prior Publication Data

US 2015/0059434 A1    Mar. 5, 2015

(30) Foreign Application Priority Data

Aug. 29, 2013  (IN) .......................... 3838/CHE/2013

(51) Int. Cl.
*G01N 33/18* (2006.01)
*G01N 21/17* (2006.01)
(Continued)

(52) U.S. Cl.
CPC ..... *G01N 21/1702* (2013.01); *G01N 29/2418* (2013.01); *G01N 29/2425* (2013.01);
(Continued)

(58) Field of Classification Search
CPC ............... G01N 21/1702; G01N 21/39; G01N 33/2841; G01N 29/2418
(Continued)

(56) References Cited

U.S. PATENT DOCUMENTS 6,121,627 A   9/2000 Tulip
6,585,938 B1  7/2003 Machida et al.
(Continued)

FOREIGN PATENT DOCUMENTS

DE   10308409 A1   9/2004
EP    2256479 A2  12/2010
(Continued)

OTHER PUBLICATIONS

High Voltage Engineering and Application, "Study on the Gas Pressure Characteristics of Photoacoustic Spectroscopy Detection for Dissolved Gases in Transformer Oil", Fu Wan, Weigen Chen, Xiajuan Peng, Jing Shi, Sep. 2012, pp. 286-289.

(Continued)

*Primary Examiner* — Benjamin Schmitt
(74) *Attorney, Agent, or Firm* — GE Global Patent Operation; Scott R. Stanley

(57) ABSTRACT

A method for detecting of components in a fluid includes emitting a modulated light beam from a modulated light source to the fluid in a chamber, wherein the fluid comprises a liquid and a component in the liquid. The method includes producing an acoustic signal in response to the emitted modulated light beam and detecting the acoustic signal via a pressure sensor disposed in the chamber. The method in one example also includes transmitting the acoustic signal from the pressure sensor to a processor based module and determining at least one of a component and a concentration of the component in the fluid via the processor based module, based on the acoustic signal.

16 Claims, 9 Drawing Sheets

(51) Int. Cl.
*G01N 29/24* (2006.01)
*G01N 29/46* (2006.01)
*G01N 29/48* (2006.01)

(52) U.S. Cl.
CPC ............. *G01N 29/46* (2013.01); *G01N 29/48* (2013.01); *G01N 2021/1704* (2013.01); *G01N 2021/1708* (2013.01); *G01N 2201/067* (2013.01); *G01N 2201/06113* (2013.01); *G01N 2291/02433* (2013.01); *G01N 2291/02809* (2013.01)

(58) Field of Classification Search
USPC .................................... 73/19.03, 19.1, 19.11
See application file for complete search history.

(56) References Cited

U.S. PATENT DOCUMENTS

| | | | |
|---|---|---|---|
| 7,924,423 | B2 | 4/2011 | Van Neste et al. |
| 8,102,532 | B2 | 1/2012 | Kosterev et al. |
| 2006/0192122 | A1* | 8/2006 | Chen .................. G01N 21/0332 250/339.13 |
| 2010/0027012 | A1* | 2/2010 | Fritz .................. G01N 21/1702 356/432 |
| 2011/0016962 | A1 | 1/2011 | DiFoggio |
| 2011/0023594 | A1 | 2/2011 | Pelletier et al. |
| 2012/0300210 | A1 | 11/2012 | Dong et al. |

FOREIGN PATENT DOCUMENTS

| | | |
|---|---|---|
| WO | 2008103837 A1 | 8/2008 |
| WO | 2012110588 A1 | 8/2012 |
| WO | 2014132046 A2 | 9/2014 |

OTHER PUBLICATIONS

European Search Report and Written Opinion issued in connection with corresponding EP Application No. 14181831.0 dated Sep. 28, 2015.

* cited by examiner

METHOD AND SYSTEM FOR DETECTING A COMPONENT IN A FLUID

BACKGROUND

The subject matter disclosed herein generally relates to detection systems and in particular, to detection systems for measuring at least one of a component and a concentration of the component in a fluid using photo acoustic spectroscopy (PAS) techniques.

Electrical equipment, such as transformers, typically use fluids having good thermal and insulation properties to encapsulate parts of the electrical equipment in a containment vessel, for enabling dissipation of heat generated from the coils. The fluid may be oil such as castor oil, mineral oil, synthetic oil such as chlorinated diphenyl silicone oil, and the like.

Failure of electrical equipment, such as coils of a transformer, may result in disruption of operation. Monitoring of the electrical equipment to predict potential failures of the equipment through detection of incipient faults is hence desirable. A known method of monitoring the electrical equipment involves analysis of various parameters of the transformer fluid. Presence of total combustible gas (TCG) in the fluid is known to provide information about operating states of the electrical equipment immersed in the fluid. To enable early detection of faults in one example, the dissolved gases, within the fluid are analyzed. Presence and concentrations of gaseous components such as carbon monoxide, carbon dioxide, and the like may be indicative of thermal aging of the equipment. Similarly, gaseous components such as hydrogen, hydrocarbons, and the like may be indicative of a dielectric breakdown among other faults.

Known methods such as Gas Chromatography (GC), Optical Spectroscopy, and Photo Acoustic Spectroscopy (PAS) for analyzing dissolved gases, require the extraction of gases from the fluid. The known extraction techniques such as vacuum extraction, and head space extraction methods suffer from drawbacks such as repeatability issues and increased complexity There is therefore a need for enhanced techniques to measure at least one of a component and a concentration of the component in a fluid that is uncomplicated and repeatable.

BRIEF DESCRIPTION

In accordance with one aspect, systems for detecting components in fluids are disclosed. The system in one example includes a chamber having the fluid including a liquid and a component in the fluid. The system also includes a modulated light source for emitting a modulated light beam to the fluid, to generate an acoustic signal due to the presence of the component. The system further includes a pressure sensor disposed in the chamber, for detecting the acoustic signal and a processor based module communicatively coupled to the pressure sensor and configured to receive the acoustic signal from the pressure sensor and determine at least one of a component and a concentration of the component in the fluid based on the acoustic signal.

In accordance with another aspect, a method for detecting components in a fluid is disclosed. The method includes generating a modulated light beam from a modulated light source and emitting it to the fluid in a chamber, wherein the fluid comprises a liquid and a component in the liquid. The method includes producing an acoustic signal from the component in the chamber, in response to the emitted modulated light beam and detecting the acoustic signal via a pressure sensor disposed in the chamber. The method also includes transmitting the acoustic signal from the pressure sensor to a processor based module and determining at least one of a component and a concentration of the component in the fluid via the processor based module, based on the acoustic signal.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Embodiments of the present disclosure relate to systems and methods for detecting the presence of components in a fluid using spectroscopic methods. Specifically, in certain embodiments, the composition and concentration of a dissolved gas in a liquid is determined using photo acoustic spectroscopy (PAS) techniques. In one example, a light beam from a modulated light source having a first beam wavelength and a second beam wavelength is emitted to a fluid in a chamber. A pressure sensor disposed in the chamber measures an acoustic signal generated in the chamber. A processor based module which is communicatively coupled to the pressure sensor, receives the acoustic signal and determines at least one of a component and a concentration of the component in the fluid based on the acoustic signal.

Figure 1:
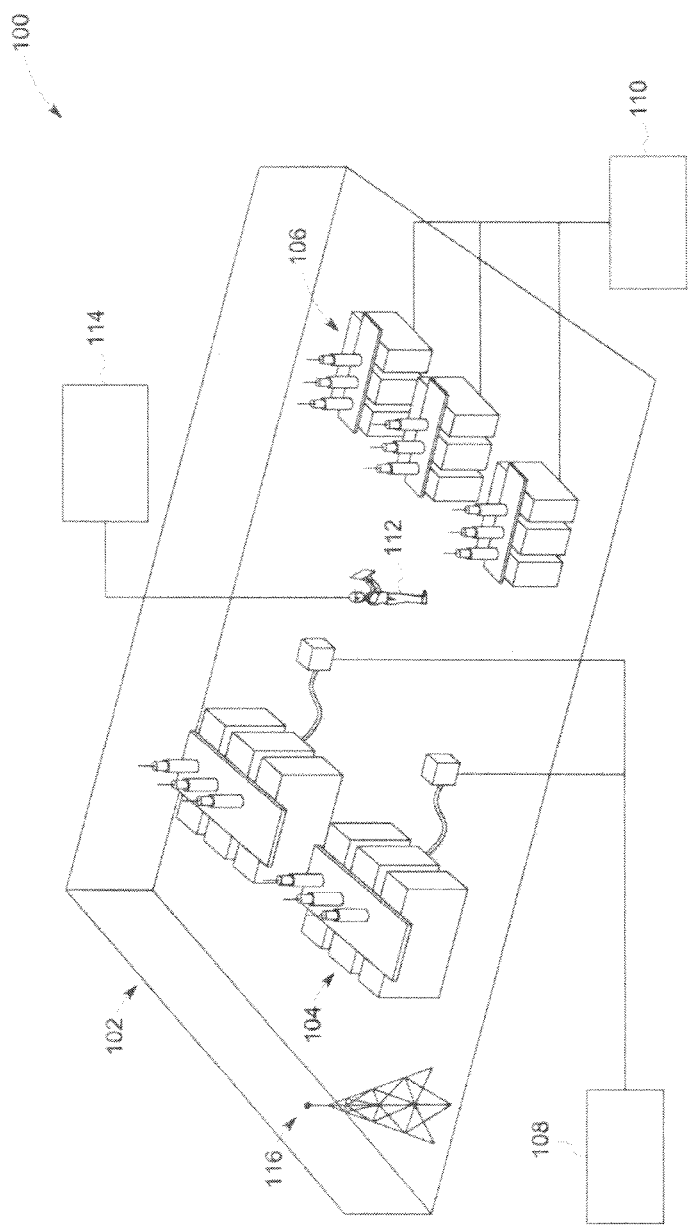
FIG. 1 is a diagrammatic illustration of an electrical utility monitored in accordance with an exemplary embodiment.

FIG. 1 illustrates an electrical utility 100 incorporating an exemplary system for inspection of equipment disclosed therein. The electrical utility 100 has an electrical infrastructure 102 having equipment 104, 106 which are to be inspected. In the illustrated embodiment, the equipment 104, 106 are transformers. The equipment 104 is monitored by an exemplary inspection system 108 and the equipment 106 is monitored by another exemplary inspection system 110. Further, a portable diagnostic subsystem 114 may be used by a mobile operator 112 for quick and accurate diagnostics of the health of the equipment 104, 106. Additionally, the electrical utility 100 may also be equipped with a remote monitoring and diagnostic subsystem 116 for providing continuous asset monitoring capability. The remote monitoring in one example, involves online fault monitoring and trending of faults to predict failure of the equipment 104, 106. It should be noted herein that the illustrated electrical utility 100 should not be construed as a limitation. In other words, the exemplary inspection systems 108, 110 are applicable for other applications and equipment in which there is a requirement for detecting the presence of a component in a fluid.

Figure 2:
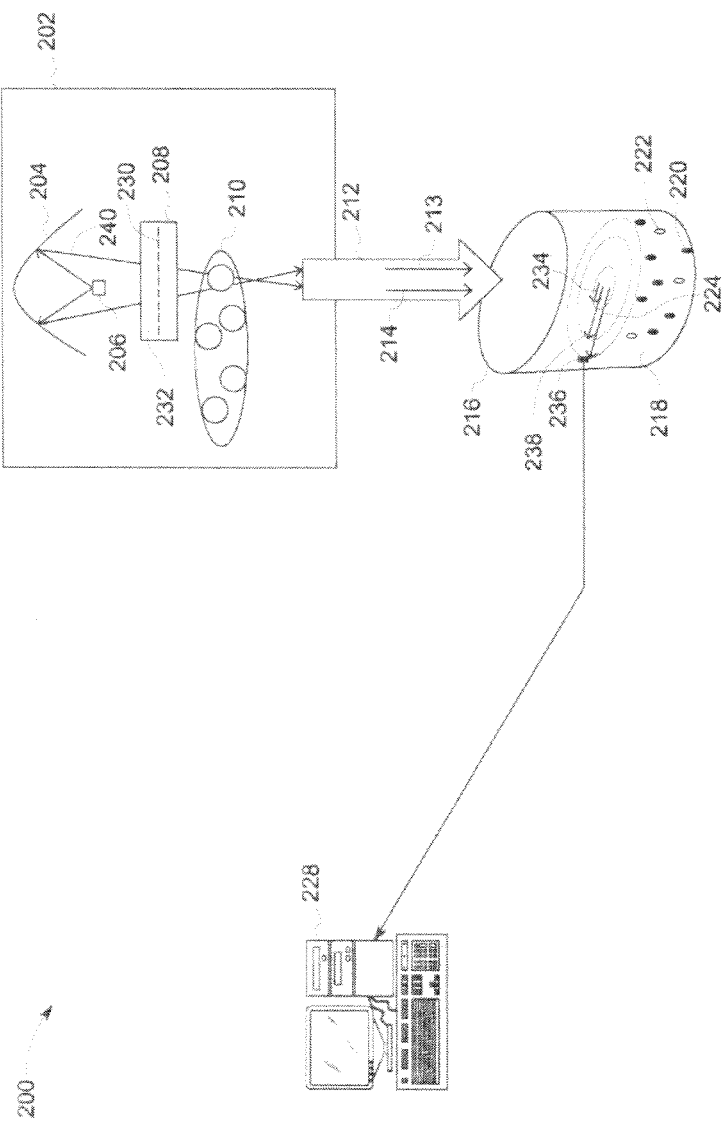
FIG. 2 illustrates a detection system in accordance with an exemplary embodiment.

FIG. 2 illustrates a detection system 200 used in at least one of the inspection systems 108, 110 (shown in FIG. 1) in accordance with an exemplary embodiment. The detection system 200 includes a modulated light source 202 for emitting a modulated light beam 212 to a fluid 218 filled in a chamber 216 to generate an "acoustic signal" 224. The "acoustic signal" 224 referred to herein relates to pressure signals generated by fluctuations in temperature of the fluid 218 due to the modulated light beam 212. In the illustrated embodiment, the modulated light source 202 includes a light source 206 for generating a light beam 240 and a modulator device 208 for generating the modulated light beam 212. In one embodiment, the light source 206 is a laser light source. In other embodiments, the light source 206 is a broad band light source, a tunable diode (TD) laser source, or a quantum cascade laser source.

The modulator device 208 modulates the light beam 240 by controlling at least one of an intensity of the light beam 240, a wavelength of the light beam 240, and a parameter of the light source 206. In the illustrated embodiment, the modulator device 208 is a chopper having a rotatable disc 230 with a plurality of slots 232. The rotatable disc 230 is used for generating the modulated light beam 212 in the form of light pulses. In other embodiments, the modulator device 208 is used to modulate the intensity of the light beam 240 by other suitable techniques. In one specific embodiment, the modulator device 208 is used to modulate the wavelength of the light beam 240. In some embodiments, the modulator device 208 is a part of the light source 206 and a direct modulation technique is employed. In such embodiments, the light beam 240 is modulated by varying a parameter of the light source 206. In one embodiment, ambient temperature of the light source 206 is modified to generate the modulated light beam 212. In another embodiment, input power to the light source 206 is varied to generate the modulated light beam 212. The modulated light beam 212 has a range of wavelength suitable for detecting the presence of one or more components in the fluid 218.

In the illustrated embodiment, the modulated light source 202 includes a reflector 204 and the light source 206. The light source 206 generates a light beam that strikes the reflector 204 and produces a reflected light beam 240. The modulated light source 202 also includes an optical filter 210 for filtering the light beam 240 corresponding to the desired wavelength. In a specific embodiment, the optical filter 210 includes a plurality of filters having different wavelengths. The optical filter 210 receives the modulated light beam and generates a first beam wavelength 213 and a second beam wavelength 214. In other embodiments, alternate configurations of the optical elements may be used to generate the modulated light beam 212. For example, there may be multiple beam wavelengths using multiple optical filters 210 at approximately the same time and/or having different wavelengths at different times using different filters.

In the illustrated embodiment, the fluid 218 includes a component 222 dissolved in a liquid 220. In an exemplary embodiment, the liquid 220 is a sample of insulation oil used in the equipment to be inspected, for example, a transformer. The component 222 may be at least one of a gaseous component such as acetylene, hydrogen, methane, ethane, ethylene, carbon dioxide, carbon monoxide, moisture, and the like. In other embodiments, the fluid may be a suspension having a component suspended in a liquid. The component may be a gas, a liquid or a solid. The first beam wavelength 213 and the second beam wavelength 214 are selected based on the liquid 220 and the type of the component.

In the illustrated embodiment, the first beam wavelength 213 and the second beam wavelength 214 are determined based on the absorption spectrum of the liquid 220 and the absorption spectrum of the component 222 respectively. In one embodiment, the first beam wavelength 213 or the second beam wavelength 214 is within a plurality of wavelengths in an absorption spectrum of the component 222. In such an embodiment, the first beam wavelength 213 and the second beam wavelength 214 are within a plurality of wavelengths in an absorption spectrum of the liquid 220. The first beam wavelength 213 and the second beam wavelength 214 are generated in such a manner so as to generate the acoustic signal 224. The generation of the first beam wavelength 213 and the second beam wavelength 214 are explained in detail with reference to subsequent figures.

In this example, the acoustic signal 224 generated in the chamber 216, includes a first acoustic signal 234 generated due to the presence of the liquid 220 and a second acoustic signal 238 generated due to the presence of the component 222. The liquid 220 absorbs different amounts of light energy from the first beam wavelength 213 and the second beam wavelength 214. The difference in the absorption of light energy generates a fluctuation in temperature of the liquid 220. The "first acoustic signal" 234 referred herein is a pressure signal generated due to the fluctuation in temperature of the liquid 220, wherein the fluctuation is caused by the modulated light beam 212.

The component 222 absorbs different amounts of light energy from the first beam wavelength 213 and the second beam wavelength 214. The difference in the absorption of the light energy generates a fluctuation in temperature of the component 222. A "second acoustic signal" 238 is a pressure signal generated due to fluctuation in temperature of the component 222, wherein the fluctuation is caused by the modulated light beam 212. The first beam wavelength 213 and the second beam wavelength 214 of the modulated light beam 212 are chosen such that the first acoustic signal 234 has a smaller amplitude compared to the second acoustic signal 238. The acoustic signal 224 is approximately equal to the second acoustic signal 238 due to the presence of the component 222.

In an alternate embodiment, the first acoustic signal 234 is comparable to the second acoustic signal 238. In such a scenario, the second acoustic signal 238 is not approximately equal to the acoustic signal 224. If an estimate of the first acoustic signal 234 is available, then an estimate of the second acoustic signal 238 is obtained by subtracting the estimate of the first acoustic signal 234 from the acoustic signal 224. An estimate of the first acoustic signal 234 may be obtained by a separate experiment. In an exemplary embodiment, a first beam wavelength and a second beam wavelength are emitted to a liquid and an acoustic signal corresponding to a first acoustic signal is measured via a pressure sensor.

A pressure sensor 236 is disposed proximate the chamber 216 to detect the acoustic signal 224. In one embodiment, the pressure sensor 236 is disposed at the bottom of the chamber 216. In another embodiment, the pressure sensor 236 is disposed at the middle of the chamber 216. In another embodiment, the pressure sensor 236 is disposed on the outer surface of the chamber 216. In an exemplary embodiment, the pressure sensor 236 is disposed so as to detect maximum amplitude of the acoustic signal 224. In another exemplary embodiment, the pressure sensor 236 is disposed so as to detect the acoustic signal 224 with a high signal to noise ratio (SNR).

In one embodiment, the pressure sensor 236 is a piezo-based pressure sensor. In such an embodiment, the pressure sensor 236 may employ a piezo-electric effect or a piezo-resistance effect to detect the acoustic signal 224. In certain other embodiments, the pressure sensor 236 may be a cantilever-based pressure sensor, a microphone, a hydrophone, a capacitance based sensor, a magnetic fluid based sensor, or a membrane based pressure sensor.

A processor-based module 228 is communicatively coupled to the pressure sensor 236 and configured to receive the acoustic signal 224 from the pressure sensor 236. The processor-based module 228 is further configured to determine at least one of a component and a concentration of the component 222 in the fluid 218 based on at least one of an amplitude, a frequency and phase information of the acoustic signal 224.

The processor-based module 228 may include a controller, a general purpose processor, multi-core processors, or an embedded system. The processor-based module 228 may receive additional inputs from a user through an input device such as a keyboard or a control panel. The processor-based module 228 may also be communicatively coupled to a memory module such as a random access memory (RAM), read only memory (ROM), flash memory, or other type of computer readable memory. Such a memory module may be encoded with a program to instruct the processor-based module 228 to enable a sequence of steps to determine at least one of a component and the concentration of the component 222. In certain embodiments, all the components of the exemplary detection system 200 may be incorporated as a single stand-alone module integrated with the inspection systems 108, 110 (shown in FIG. 1).

Figure 3:
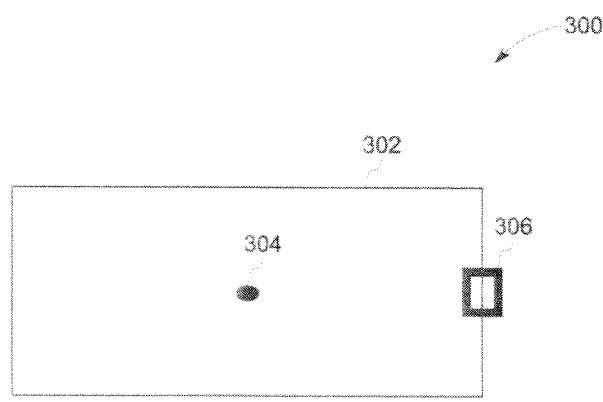
FIG. 3 illustrates relative position of a center of a pressure wave front and a pressure sensor in accordance with an exemplary embodiment.

FIG. 3 is a schematic diagram 300 illustrating relative positions of a center of a pressure wave front and a pressure sensor in accordance with an exemplary embodiment. In the illustrated embodiment, a rectangle 302 is representative of a chamber and a point 304 is representative of a location in the chamber at which the modulated light beam is emitted to a fluid in the chamber. The fluid in the chamber may have one or more components. Specifically, the point 304 is indicative of approximately the center of the pressure wave front generated in the fluid due to the emission of the modulated light beam. In the illustrated embodiment, the pressure sensor is disposed at a position 306 with reference to the rectangle 302. Although, in the illustrated embodiment, the center of the pressure wave is represented as the point 304, in other embodiments, the pressure wave may also be generated along a line by emitting the modulated light beam along the line to the fluid filled in the chamber.

Although the chamber 302 is depicted as a rectangle, the shape and size are subject to design criteria and the chamber can be cylindrical, squared, polygonal and the like. It can vary in size depending upon the implementation, provided that there is sufficient liquid and component to perform the measurement for presence and concentration.

Figure 4:
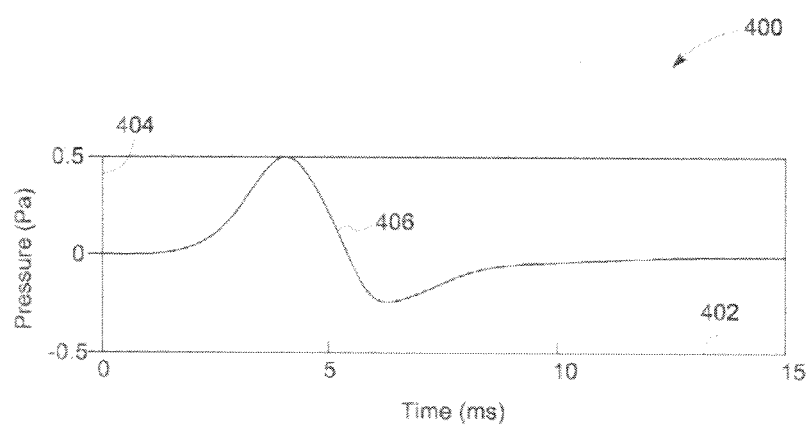
FIG. 4 illustrates a graph showing variation of a pressure waveform detected by a pressure sensor in accordance with an exemplary embodiment.

FIG. 4 illustrates a graph 400 showing variation of a pressure wave front in accordance with an exemplary embodiment of FIG. 3. The x-axis 402 of the graph 400 is representative of the time in microseconds and the y-axis 404 of the graph 400 is representative of pressure in Pascal. A waveform 406 is representative of a variation in the pressure wave detected by the pressure sensor disposed at the position 306. The waveform 406 is normalized and representative of the impulse response of the fluid.

Figure 5:
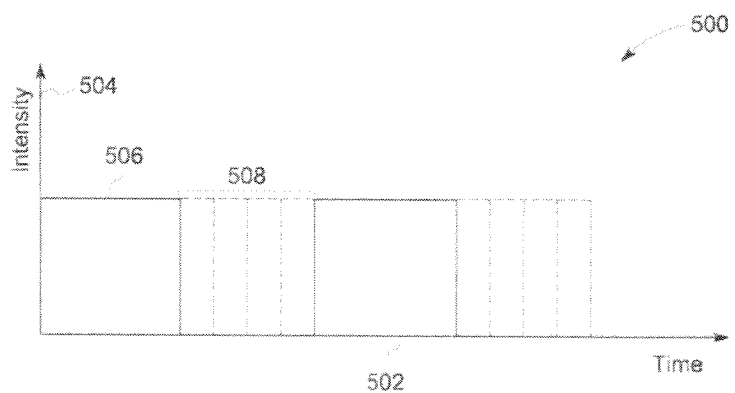
FIG. 5 illustrates graph showing a modulated light beam in accordance with an exemplary embodiment.

FIG. 5 illustrates a graphical representation 500 of a variation in intensity of a modulated light beam 212 in accordance with an exemplary embodiment of FIG. 2. The x-axis 502 of the graph 500 is representative of the time and the y-axis 504 of the graph 500 is representative of the intensity (output power in milli watts) of the modulated light beam 212. The graph 500 illustrates a first pulse 506 of the modulated light beam 212 at a first time slot and a second pulse 508 of the modulated light beam 212 at a second time slot. The first pulse 506 has the first beam wavelength 213 and the second pulse 508 has the second beam wavelength 214. In the illustrated embodiment, the first pulse 506 and the second pulse 508 are generated alternately.

It should be noted herein that either the first beam wavelength 213 or the second beam wavelength 214 is within a plurality of wavelengths in the absorption spectra of the component 222. Thus, if the first beam wavelength 213 is within a plurality of wavelengths in the absorption spectra of the component 222, the component 222 absorbs the light energy when the first pulse 506 is transmitted to the fluid 218 and the light energy is not absorbed by the component 222 when the second pulse 508 is transmitted to the fluid 218. If the second beam wavelength 214 is within a plurality of wavelengths in the absorption spectra of the component 222, the component 222 absorbs the light energy when the second pulse 508 is transmitted to the fluid 218 and the light energy is not absorbed by the component 222 when the first pulse 506 is transmitted to the fluid 218. Both the first beam wavelength 213 and the second beam wavelength 214 are within a plurality of wavelengths in the absorption spectra of the liquid 220. The liquid 220 absorbs the same or almost same amount of light energy when the first pulse 506 or the second pulse 508 is transmitted to the fluid 218. In another embodiment, both the first beam wavelength 213 and second beam wavelength 214 are within a plurality of wavelengths in the absorption spectra of the component 222. The component 222 absorbs a first amount of light energy when the first beam wavelength 213 is transmitted to the fluid 218 and a second amount of light energy different from the first amount of energy when the second beam wave length 214 is transmitted to the fluid 218.

In other embodiments, the first pulse 506 and the second pulse 508 may have a different shape and/or emitted at different time slots. In certain embodiments, the first pulse 506 and the second pulse 508 may have varying intensities with respect to the corresponding time slots. In some embodiments, the first pulse 506 may have a non-zero value at the second time slot and the second pulse 508 may have a non-zero value at a first time slot. The first pulse 506 and the second pulse 508 may overlap in time. The first pulse 506 and the second pulse 508 may be amplitude modulated, frequency modulated, or phase modulated. In some embodiments, the modulated light beam 212 is generated using a combination of modulation techniques such as amplitude modulation, frequency modulation, and phase modulation. In one embodiment, the first beam wavelength and the second beam wavelength are amplitude modulated based on a first amplitude and a second amplitude respectively. The first beam wavelength has the first amplitude and the second beam wavelength has the second amplitude different from the first amplitude. The modulation techniques facilitate generation of a pressure wave caused by the component during the simultaneous emission of the modulated light beam having the first beam wavelength and the second wavelength.

Figure 6:
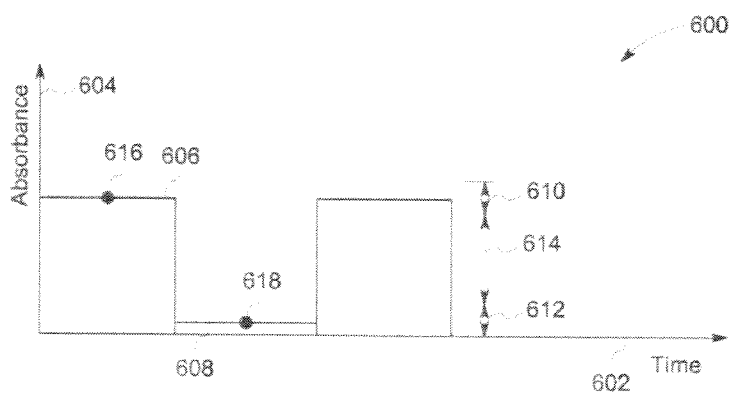
FIG. 6 illustrates a graph representative of an absorbance of a component in a fluid in accordance with an exemplary embodiment.

FIG. 6 illustrates a graph 600 representative of a variation in absorbance of a component in a fluid in accordance with an exemplary embodiment. The x-axis 602 of the graph 600 is representative of time and the y-axis 604 of the graph 600 is representative of absorbance which is a ratio indicative of the radiation absorbed by the component. When the first pulse is transmitted, the component absorbs light energy from the modulated light beam having the first beam wavelength. When the second pulse is transmitted, the component absorbs a different amount of light energy from the modulated light beam having the second beam wavelength. One among the first beam wavelength and the second beam wavelength has a first absorption value 616 within the absorption spectra of the component. The other among the first beam wavelength and the second beam wavelength has a second absorption value 618 within the absorption spectra of the component. In the illustrated embodiment, a curve 606 is representative of a high absorption value of the component. The curve 608 is representative of a low absorption value of the component. The component is subjected to a fluctuation in temperature due to variation in the energy absorption when the first pulse and the second pulse are transmitted to the fluid. Such a temperature variation results in a pressure wave and an acoustic signal is generated in the fluid due to the presence of the component.

In one embodiment, the component has the first absorption value 616 within a first range 610 of absorption values in the absorption spectra of the component for one beam wavelength among the first beam wavelength and the second beam wavelength. In such an embodiment, the component has the second absorption value 618 within a second range 612 of absorption values in the absorption spectra of the component for the other beam wavelength among the first beam wavelength and the second beam wavelength. It should be noted herein that the second range 612 is different from the first range 610. The first range 610 corresponds to the high absorption value of the curve 606 and the second range 612 corresponds to the low absorption value of the curve 608. A separation 614 between the first range 610 and the second range 612 generates the fluctuation in temperature of the component due to the emission of the modulated light beam to the fluid.

Figure 7:
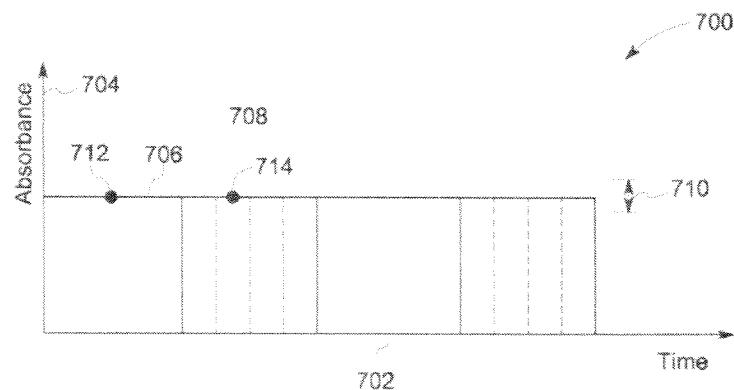
FIG. 7 illustrates a graph representative of an absorbance of a liquid in accordance with an exemplary embodiment.

FIG. 7 illustrates a graph 700 representative of a variation in absorbance of a liquid in a fluid in accordance with an exemplary embodiment. The x-axis 702 of the graph 700 is representative of time and the y-axis 704 of the graph 700 is representative of absorbance. When the first pulse is transmitted, the liquid absorbs energy from the modulated light beam having the first beam wavelength. The curve 706 is representative of a high absorption value of the liquid during the first pulse. When the second pulse is transmitted, the liquid absorbs same or substantially same amount of energy from the modulated light beam having the second beam wavelength. The curve 708 is representative of a high absorption value of the liquid when the second pulse is transmitted.

Both the first beam wavelength and the second beam wavelength have a plurality of absorption values within absorption spectra of the liquid. The plurality of absorption values includes a third absorption value 712 for one among the first beam wavelength and the second beam wavelength. The plurality of absorption values further includes a fourth absorption value 714 for the other among the first beam wavelength and the second beam wavelength. When the third absorption value 712 is exactly same as the fourth absorption value 714, the temperature of the liquid does not vary and no acoustic signal is generated due to the presence of the liquid. When the third absorption value 712 is substantially same as the fourth absorption value 714, the temperature of the liquid varies to a small extent and an acoustic signal with a relatively smaller magnitude compared to the acoustic signal due to the component is generated due to the presence of the liquid 220.

In some embodiments, the first beam wavelength and the second beam wavelength have a plurality of absorption values within a range 710 of absorption values within absorption spectra of the liquid. The third absorption value 712 and the fourth absorption value 714 are included in the range of absorption values 710. Variations in energy absorption by the liquid results in a variation in the temperature of the liquid, thereby resulting in generation of an acoustic signal due to the presence of the liquid. The variation in temperature of the liquid is dependent on the range 710. It should be noted herein, that the variation in temperature due to the presence of the liquid is lower in magnitude compared to the variation in temperature due to the presence of the component 222. In one embodiment, the first acoustic signal 234 (shown in FIG. 2) is at least 60 dB lower compared to the second acoustic signal 238 (shown in FIG. 2). In other embodiments, the first acoustic signal is lower than the second acoustic signal by an amplitude in the range of 40-100 dB. In an alternate embodiment, the variation in temperature of the liquid 220 and the variation in temperature of the component 222 are comparable. In such an embodiment, the first acoustic signal 234 and the second acoustic signal 238 have similar values.

Figure 8:
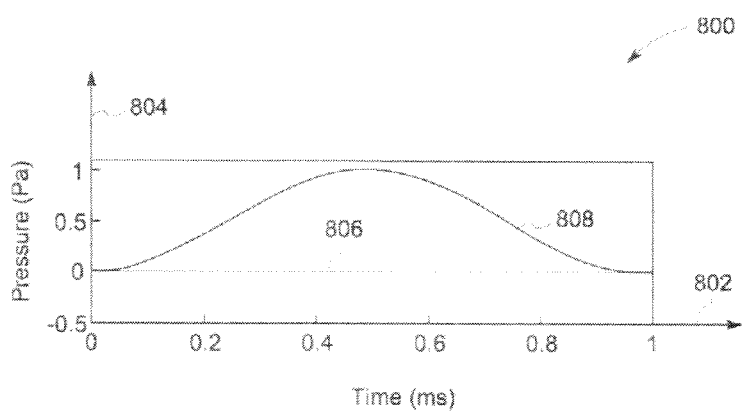
FIG. 8 illustrates of a graph representative of acoustic signals corresponding to a liquid and a component of a fluid respectively in accordance with an exemplary embodiment.

FIG. 8 illustrates a graph 800 representative of an acoustic signal generated due to presence of a liquid of a fluid in accordance with an exemplary embodiment. The x-axis 802 of the graph 800 is representative of time in milliseconds and the y-axis 804 of the graph 800 is representative of pressure values of the acoustic signal. A straight line curve 806 is representative of the acoustic signal generated due to the presence of the liquid and a curve 808 is representative of the acoustic signal generated due to the presence of the component in the fluid. The curve 806 indicates that there is insignificant acoustic signal response due to the presence of the liquid.

Figure 9:
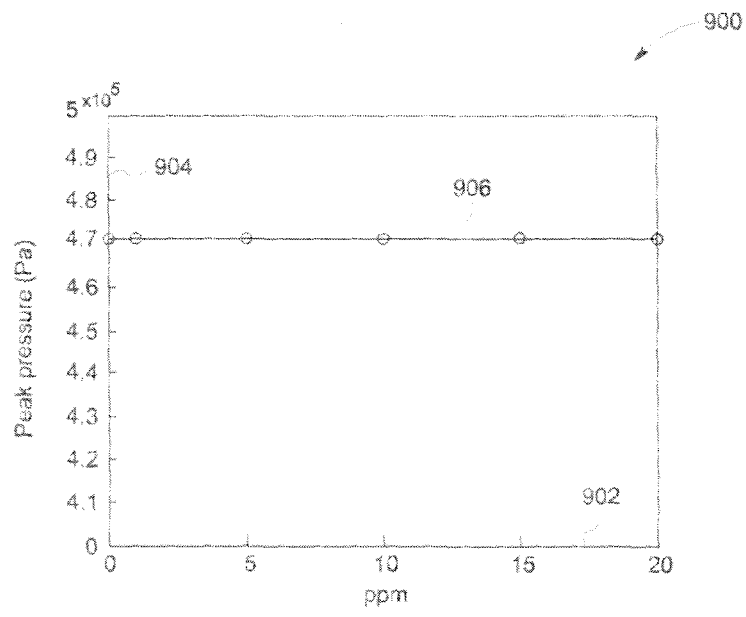
FIG. 9 is a graph representative of a variation in amplitude of a photo acoustic pressure wave corresponding to a fluid comprising a liquid and a component in accordance with an exemplary embodiment.

FIG. 9 illustrates a graph 900 showing variation of amplitude of a photo acoustic pressure wave generated in the fluid due to presence of a liquid and component in accordance with an exemplary embodiment. In the graph 900, the x-axis 902 is representative of a concentration in ppm (parts per million) of the component and the y-axis 904 is representative of a peak pressure in Pascal. A curve 906 is representative of the amplitude of the photo acoustic pressure wave generated. It may be noted herein that in the illustrated embodiment, the pressure amplitude value of $4.7 \times 10^5$ Pa due to the presence of the liquid is higher compared to the amplitude of the photo acoustic pressure wave generated due to the presence of the component in accordance with the embodiment shown in the subsequent FIG. 10.

Figure 10:
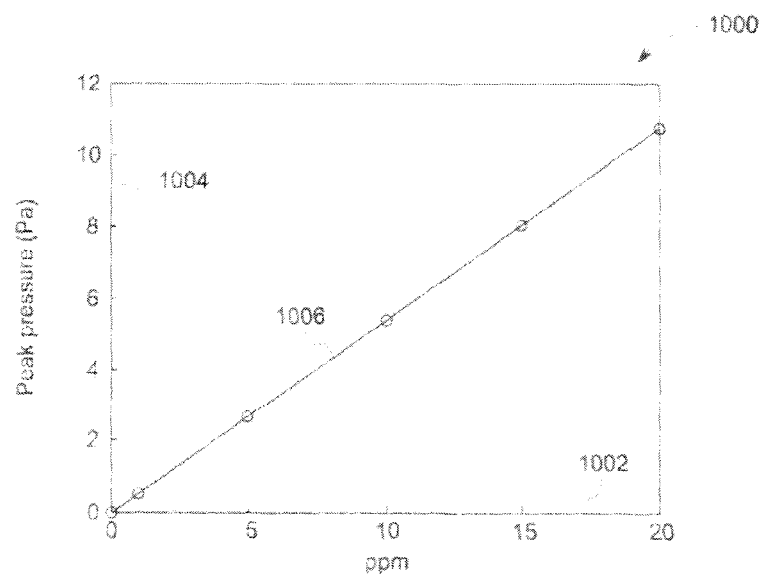
FIG. 10 is a graph representative of a variation in amplitude of a photo acoustic pressure wave corresponding to a component in a fluid in accordance with an exemplary embodiment.

FIG. 10 illustrates a graph 1000 representative of variation of amplitude of a photo acoustic pressure wave generated due to the presence of the component in the fluid in accordance with an exemplary embodiment. In the graph 1000, the x-axis 1002 is representative of concentration in ppm (parts per million) and the y-axis 1004 is representative of peak pressure in Pascal. A curve 1006 is representative of the amplitude of the photo acoustic pressure wave generated due to the presence of the component. In the illustrated embodiment, the pressure amplitude value corresponding to the curve 1006 is in the range of 0 Pa-12 Pa which is very small compared to the pressure amplitude value of the liquid discussed with reference to FIG. 9.

Figure 11:
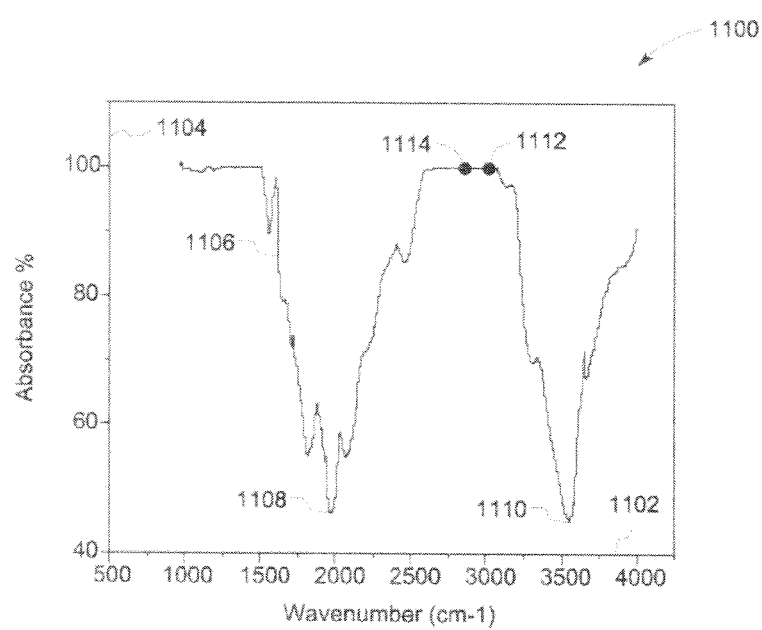
FIG. 11 is a graph representative of an absorption spectrum of a liquid in accordance with an exemplary embodiment.

FIG. 11 illustrates a graph 1100 representative of an absorption spectrum corresponding to an insulation oil (with a 0.5 mm of path length) of a transformer system, for example, in accordance with an exemplary embodiment. The x-axis 1102 of the graph 1100 is representative of wavenumber (indicated in $cm^{-1}$) and the y-axis 1104 of the graph 1100 is representative of an absorbance in percentage of absorption values. A curve 1106 is representative of the absorption spectrum of the insulation oil having a minimum absorption value of about 50% at wavenumbers 2000 $cm^{-1}$ and 3500 $cm^{-1}$ represented by numerals 1108, 1110 respectively. In the illustrated embodiment, a first absorption value 1112 and a second absorption value 1114 are same.

Figure 12:
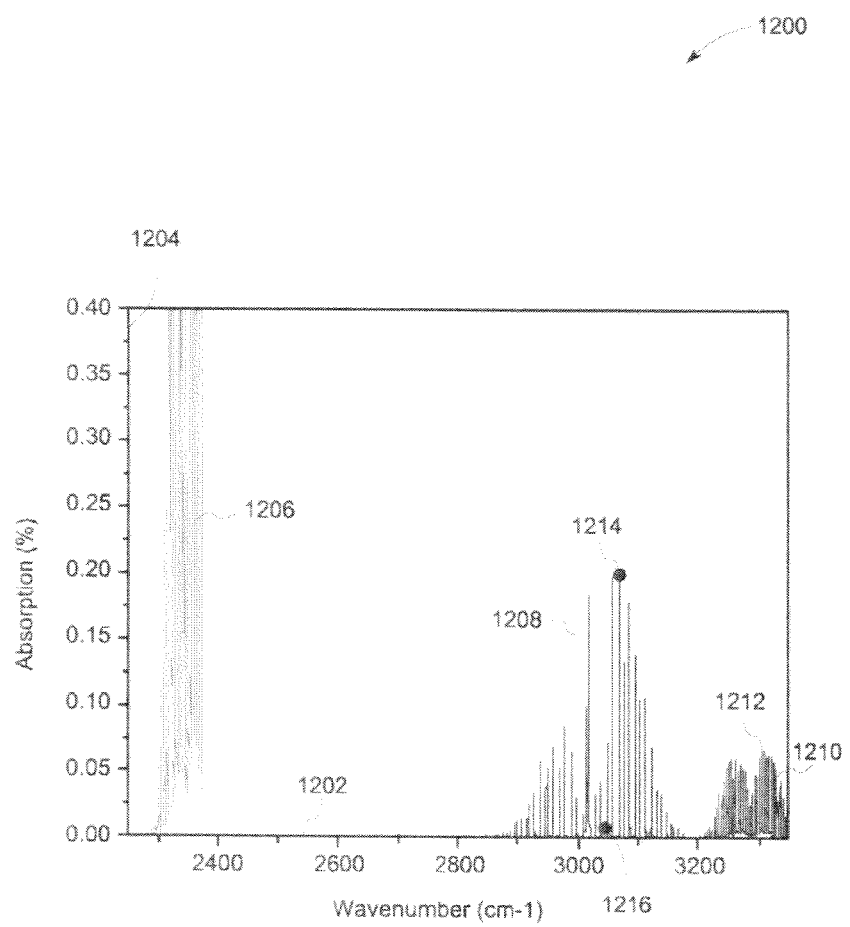
FIG. 12 is a graph representative of an absorption spectra corresponding to a plurality of gaseous components in accordance with an exemplary embodiment.

FIG. 12 illustrates a graph 1200 representative of an absorption spectra corresponding to a plurality of gaseous components (having 500 ppm, and 1 mm path length) in accordance with an exemplary embodiment. The x-axis 1202 of the graph 1200 is representative of wavenumber (in $cm^{-1}$) and the y-axis 1204 of the graph 1200 is representative of an absorbance in percentage of absorption values. The curve 1206 is representative of the absorption spectrum of carbon dioxide, the curve 1208 is representative of an absorption spectrum of methane, and the curve 1210 is representative of an absorption spectrum of acetylene. In the graph 1200, acetylene exhibits a peak absorption value of 0.05% corresponding to a wavenumber of 3300 $cm^{-1}$ represented by reference numeral 1212, methane exhibits a peak absorption value of 0.2% corresponding to a wavenumber of 3000 $cm^{-1}$ represented by reference numeral 1214, and carbon dioxide exhibits a peak absorption value of 1.4% (not shown in the graph) corresponding to wavenumber of 2300 $cm^{-1}$. In the illustrated embodiment, the third absorption value 1214 and fourth absorption value 1216 are within an absorption spectra of methane. The third absorption value 1214 is relatively higher compared to the fourth absorption value 1216. The peak absorption values corresponding to gaseous components illustrated in FIG. 12 are lower compared to the absorption value of the insulation oil at the same range of wavelength. It should be noted herein that all the values in the various embodiments discussed herein should not be construed as a limitation of the invention.

Figure 13:
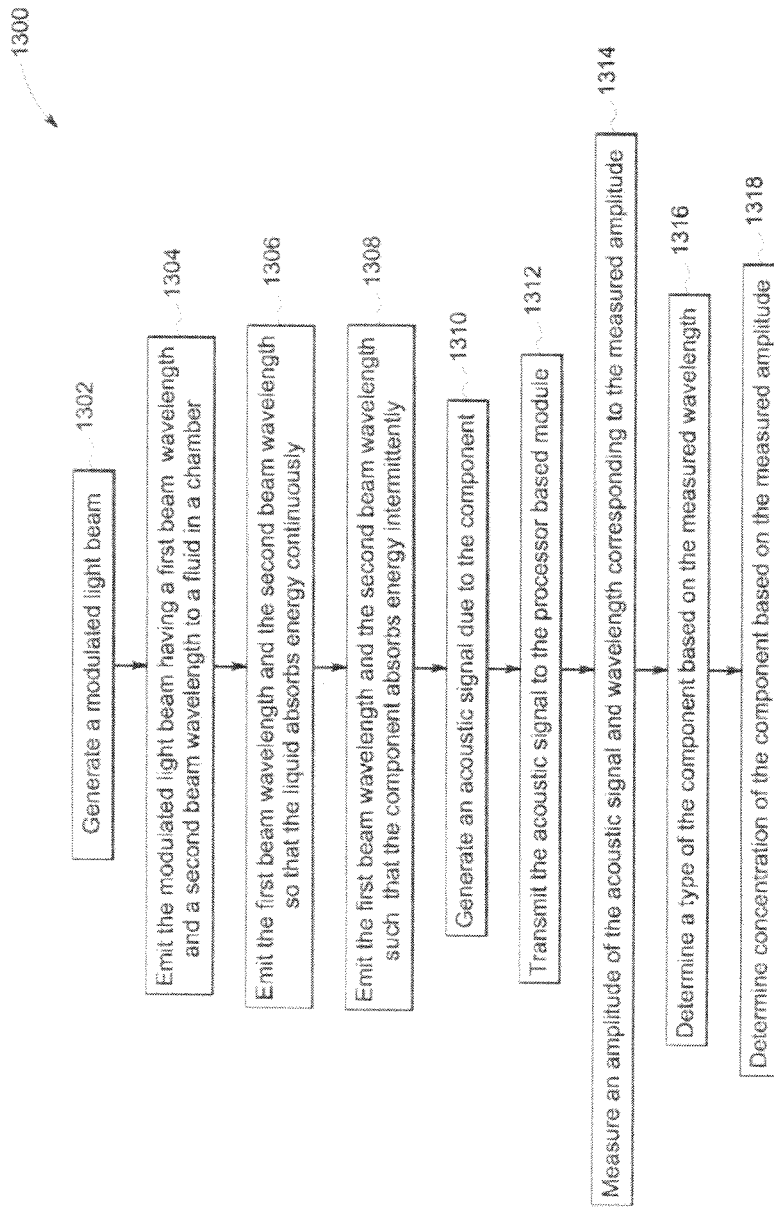
FIG. 13 is a flow chart illustrating exemplary steps involved in detecting a component dissolved in a liquid in accordance with an exemplary embodiment.

FIG. 13 is a flow chart 1300 illustrating exemplary steps of a method involved in detecting A component dissolved in the liquid in accordance with an exemplary embodiment. The method includes generating a modulated light beam 1302 by modulating at least one of an intensity and a wavelength of a light beam from a light source. The modulated light beam is emitted to a fluid in a chamber 1304. The fluid includes a liquid and a component in the liquid. In one embodiment, the fluid includes a component dissolved in a liquid. In another embodiment, the fluid is a suspension having a component suspended in a liquid. In an embodiment, a plurality of components are dissolved or suspended in the liquid. The emitted modulated light beam has a first beam wavelength and a second beam wavelength.

The modulated light beam having the first beam wavelength and the second beam wavelength are emitted to the fluid so that the liquid absorbs the light energy continuously 1306 and the component absorbs the light energy intermittently 1308. One among the first beam wavelength and the second beam wavelength is within a spectral absorption range of the component and the other among the first beam wavelength and the second beam wavelength is not in the spectral absorption range of the component.

However, both the first beam wavelength and the second beam wavelengths are within a spectral absorption range of the liquid. When the modulated light beam is emitted, a temperature of the fluid is varied due to the presence of the component thereby producing an acoustic signal 1310. The liquid absorbs energy from the modulated light beam having the first beam wavelength and the second beam wavelength. The temperature of the liquid does not change and hence no acoustic signal is generated due to the presence of the liquid. In one of the embodiment, the first beam wavelength and the second beam wavelength may be emitted alternately. In an alternate embodiment, the first beam wavelength and the second beam wavelength are amplitude modulated and overlap in time. The acoustic signal from the component is produced due to a difference between the first absorption value within the first range of absorption values and the second absorption value within the second range of absorption values in the absorption spectra of the component.

The acoustic signal may include one of an optical signal, an electrical signal, and a pressure signal based on the type of the pressure sensor used. The generated acoustic signal is then transmitted to a processor based module 1312. The processor based module measures an amplitude value of the received acoustic signal 1314. In one embodiment, the measured amplitude value of the received acoustic signal may be a peak value of the acoustic signal. In another embodiment, amplitude of the acoustic signal is determined based on a magnitude and a phase of the acoustic signal. In an exemplary embodiment, the amplitude of the acoustic signal is measured using a synchronous demodulation technique.

The processor based module determines a type of the component 1316 based on the range of wavelengths of the modulated light beam. In some embodiments, a look-up table having data corresponding to the gaseous components and their corresponding absorption spectral range may be used to determine the type of the component. In one example, if one among the first beam wavelength and the second beam wavelength of the modulated light beam corresponds to a wavenumber in the range of 2200-2400 $cm^{-1}$, the processor based module determines the component as carbon dioxide. In another example, if one among the first beam wavelength and the second beam wavelength of the modulated light beam corresponds to a wavenumber in the range of 2900-3100 $cm^{-1}$, the component is detected as methane. In yet another example, if one among the first beam wavelength and the second beam the wavelength of the modulated light beam corresponds to a wavenumber in the range of 3200-3400 cm$^{-1}$, the component is detected as acetylene. In one embodiment, a concentration of the component may be determined 1318 based on the measured amplitude using a predetermined calibration chart. In a specific embodiment, the calibration chart may be determined based on a transfer function. In another embodiment, the calibration chart may be determined based on simulation results. The calibration chart may be a look-up table having data of concentration values for a range of amplitude values corresponding to each component.

According to one example, the process can be repeated such that after detecting the presence and/or concentration of the component, the process is repeated but with a different beam wavelength such as by changing the filter shown in FIG. 2. In this manner, the presence and/or concentration of other components in the sample fluid are detected.

The exemplary system and method for inspection discussed herein enable determination of at least one of a component and a concentration of the component in a fluid using photo acoustic spectroscopy (PAS). The exemplary technique involves detecting a small amplitude photo acoustic pressure wave corresponding to the component and eliminating or substantially reducing a large amplitude acoustic signal due to the presence of the liquid which would have been generated in traditional PAS. In electrical transformer systems, for example, the exemplary technique may be used to perform analysis of dissolved gas without extracting the gas from the insulation oil.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the invention are not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the inventions may include only some of the described embodiments. Accordingly, the inventions are not to be seen as limited by the foregoing description, but are only limited by the scope of the appended claims.

What is claimed is:

1. A system, comprising:
    a chamber having a fluid including a liquid and a component in the fluid;
    a modulated light source for emitting an amplitude modulated light beam;
    a first beam wavelength and a second beam wavelength selected from the amplitude modulated light beam wherein the first beam wavelength and the second beam wavelength are generated alternatively;
    the component absorbs a first amount of light energy when the first beam wavelength is transmitted to the fluid and a second amount of light energy different from the first amount of energy when the second beam wavelength is transmitted to the fluid, and producing acoustic signals from the component;
    a pressure sensor disposed proximate the chamber, for detecting the acoustic signals; and
    a processor based module communicatively coupled to the pressure sensor and configured to receive the acoustic signals from the pressure sensor and determine at least one of the component and a concentration of the component in the fluid based on a difference in the acoustic signals.

2. The system of claim 1, wherein the component is a gaseous component.

3. The system of claim 2, wherein the gaseous component comprises acetylene, hydrogen, methane, ethane, ethylene, carbon dioxide, moisture, carbon monoxide, and combinations thereof.

4. The system of claim 1, wherein the modulated light source comprises a laser source and a modulator device.

5. The system of claim 4, wherein the modulator device receives a light beam from the laser source, and modulates the light beam.

6. The system of claim 1, wherein one of the first beam wavelength and the second beam wavelength has a first absorption value within a first range of absorption values in an absorption spectra of the component.

7. The system of claim 6, wherein another among the first beam wavelength and the second beam wavelength has a second absorption value within a second range of absorption values in the absorption spectra of the component, wherein the second range of absorption values is different from the first range of absorption values.

8. The system of claim 1, wherein both the first beam wavelength and the second beam wavelength have a plurality of absorption values within a range of absorption values in an absorption spectra of the liquid.

9. The system of claim 1, wherein the pressure sensor is at least one of a piezo effect based sensor, a cantilever based sensor, a microphone, a hydrophone, a capacitance based sensor, and a membrane based sensor.

10. The system of claim 1, wherein the modulated light source comprises a light source, at least one filter, and a modulator device for controlling at least one of an intensity of a light beam generated from the light source, a wavelength of the light beam, and a parameter of the light source.

11. A method, comprising:
    emitting an amplitude modulated light beam to a fluid in a chamber wherein the fluid comprises a liquid and a component in the liquid;
    selecting a first beam wavelength and a second beam wavelength from the amplitude modulated light beam and generating the first beam wavelength and the second beam wavelength alternatively, wherein the component absorbs a first amount of light energy when the first beam wavelength is transmitted to the fluid and a second amount of light energy different from the first amount of energy when the second beam wavelength is transmitted to the fluid, and producing acoustic signals from the component;
    producing acoustic signals from the component in response to the first beam wavelength and the second beam wavelength;
    detecting the acoustic signals via a pressure sensor disposed in the chamber;
    transmitting the acoustic signals from the pressure sensor to a processor based module;

and determining at least one of the component and a concentration of the component in the fluid via the processor based module, from a difference in the acoustic signals.

12. The method of claim 11, further comprising generating the first beam wavelength and the second beam wavelength from the amplitude modulated light beam via at least one optical filter.

13. The method of claim 11, wherein the producing comprises generating the acoustic signal from the component due to a difference between a first absorption value within a first range of absorption values and a second absorption value within a second range of absorption values in an absorption spectra of the component.

14. The method of claim 11, wherein the emitting comprises modulating an amplitude of a light beam via a modulator device.

15. The method of claim 11, wherein the emitting comprises modulating a laser beam by varying a power applied to a laser source or an ambient temperature of the laser source.

16. The method of claim 11, wherein the determining comprises one of the followings:
- measuring an amplitude of the acoustic signal;
- measuring the concentration of the component based on the measured amplitude;
- measuring the amplitude of the acoustic signal using a synchronous demodulation technique; and
- identifying the component based on a range of wavelength of the modulated light beam.

* * * * *